(12) United States Patent
Ostroff et al.

(10) Patent No.: US 9,138,501 B2
(45) Date of Patent: Sep. 22, 2015

(54) DECORATIVE AIR FRESHENER

(76) Inventors: Russell Ostroff, West Islip, NY (US); Victoria Ostroff, West Islip, NY (US)

(*) Notice: Subject to any disclaimer, the term of this patent is extended or adjusted under 35 U.S.C. 154(b) by 746 days.

(21) Appl. No.: 13/373,790

(22) Filed: Nov. 30, 2011

(65) Prior Publication Data

US 2012/0187022 A1 Jul. 26, 2012

Related U.S. Application Data

(60) Provisional application No. 61/458,734, filed on Dec. 1, 2010.

(51) Int. Cl.
*A61L 9/04* (2006.01)
*A61L 9/12* (2006.01)
*B43L 17/00* (2006.01)
*B44D 2/00* (2006.01)

(52) U.S. Cl.
CPC . *A61L 9/12* (2013.01); *B43L 17/00* (2013.01); *B44D 2/002* (2013.01)

(58) Field of Classification Search
CPC .......... A61L 9/12; B43L 17/00; B43L 17/02; B43L 17/04; B44D 2/002
USPC ...................................... 236/53–56
See application file for complete search history.

(56) References Cited

U.S. PATENT DOCUMENTS

| 4,824,707 | A | | 4/1989 | Spector |
| 4,883,692 | A | * | 11/1989 | Spector |
| 5,590,785 | A | * | 1/1997 | Seitzinger ..................... 206/575 |
| D453,374 | S | | 2/2002 | Taylor |
| 7,926,735 | B1 | * | 4/2011 | Mobley .......................... 239/53 |
| 2008/0099576 | A1 | | 5/2008 | Hart |

* cited by examiner

*Primary Examiner* — Christopher Kim
(74) *Attorney, Agent, or Firm* — Paul M. Denk

(57) ABSTRACT

A kit, containing a blotter board or other paperboard, preferably cut to a particular design, capable of holding a fragrant material, so as to enhance the aroma of the area in which the freshener locates, with the blotter or paperboard having ample space to allow any youth to mark or decorate it for display.

3 Claims, 3 Drawing Sheets

DECORATIVE AIR FRESHENER

CROSS REFERENCE TO RELATED APPLICATION

This non provisional patent application claims priority to the provisional patent application having Ser. No. 61/458,734, having filing date Dec. 1, 2010.

FIELD OF THE INVENTION

This invention relates to the field of air freshening, and more specifically pertains to the use of paperboard or other materials that can have air freshener applied to them and at the same time allow for their decoration primarily by the youth, through the use of a marker, crayon, or the like.

BACKGROUND OF THE INVENTION

Air fresheners have become widely popular in the last twenty years. They are produced in a wide range of fragrances and appealing and decorative designs. It is known that personal taste in air fresheners vary widely with some designs and fragrances appealing more to one group of the population than others. It would be desirable for an individual to be able to construct their own personalized air freshener with the fragrance and visual appeal meaningful to them. Most commercial air fresheners are made using toxic solvents and/or aerosols that are inappropriate for use in the home or by the average consumer. The average consumer, when provided with basic materials, that are non-toxic and easy to apply, will be able to construct a decorative air freshener with a fragrance, and visual design of their choosing. This is a new concept that brings and added dimension to air freshener with personalized decoration and fragrance. Children will especially appreciate the ability to make a functional and useful product that proudly displays their handiwork.

SUMMARY OF THE INVENTION

Blotter air fresheners are a popular and widely used means of eliminating odor and/or enhancing the ambience in small spaces, particularly automobiles. Such air fresheners often bear decoration in a variety of forms, including screen printing, offset printing, foils stamping, digital printing, die-cut shapes and etc.

This invention is a new concept that brings a new dimension to the air freshener, enabling consumers (particularly children) to create their own blotter air freshener with personalized decoration and fragrance. Children will especially appreciate the ability to make a functional and useful product that proudly displays their own handiwork.

DESCRIPTION OF THE PREFERRED EMBODIMENT

Figure 1:
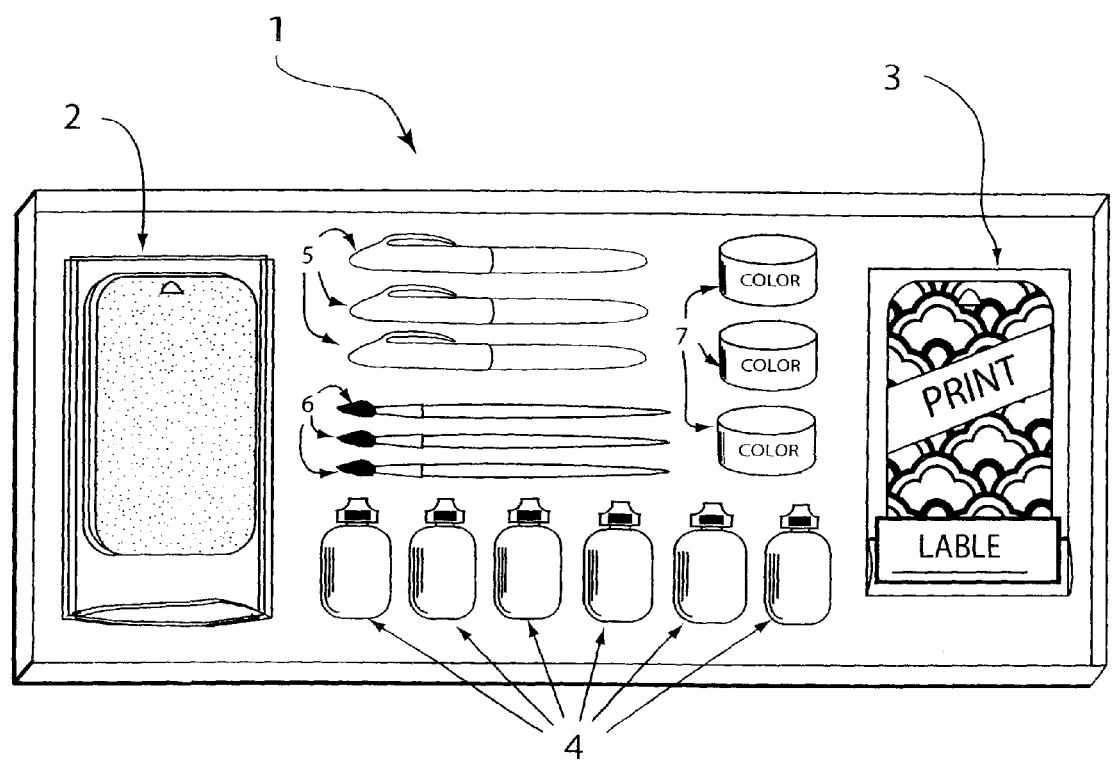
FIG. 1 illustrates one embodiment of a kit containing blotter boards in flow-wrapped plastic pouches, fragrances in sealed containers, markers, primarily crayons for writing, paint and brushes for applying color, and containers of colored paints or dyes. The kit also provides for storage of completed decorative air fresheners.
Figure 5:
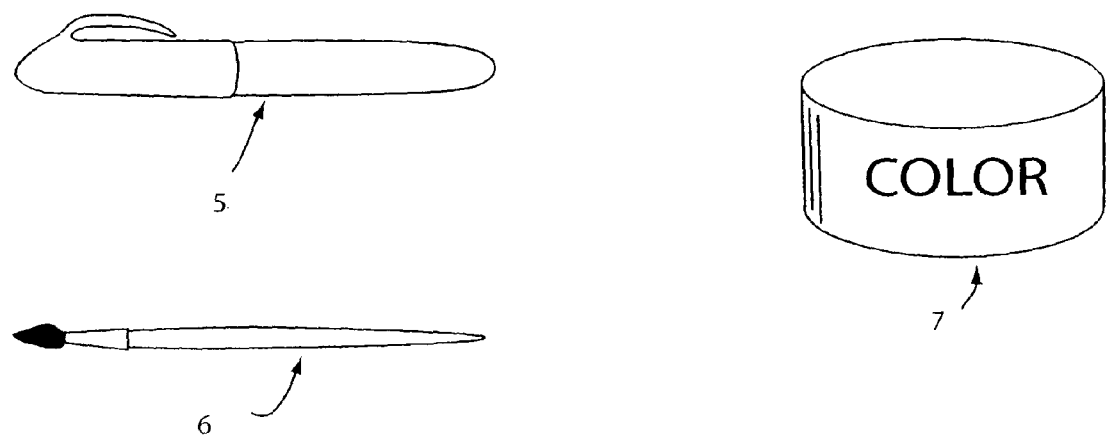
FIG. 5 illustrates embodiments of decorating instruments and materials, including a marker, mainly crayons, paint brushes, and containers of colored paints or dyes.

A preferred embodiment of the instant invention is a kit that will enable the individual to make a personalized decorative air freshener. As shown in FIG. 1, the kit 1 includes an absorbent device, preferable a blotter board 8, fragrances in sealed containers 4, as well as instruments 5, 6, and materials 7, for decorating the blotter board. Blotter boards are preferably contained within a flow-wrapped plastic pouches 2 prior to use. Fragrances are contained in single use or sealable containers. 4. The preferred kit contains various instruments and materials for decorating the blotter board to allow the individual to construct an air freshener with their own personalized fragrance and appearance. Shown in FIGS. 1 and 5 are examples of instruments and materials for decorating the absorbent device or blotter board, which include markers 5, paint brushes 6, and colored paints or dyes in sealed containers 7. The kit may also contain room for storing completed air fresheners. In sealed containers 3 shown in FIG. 1 flow-wrapped plastic pouches until use.

Figure 2:
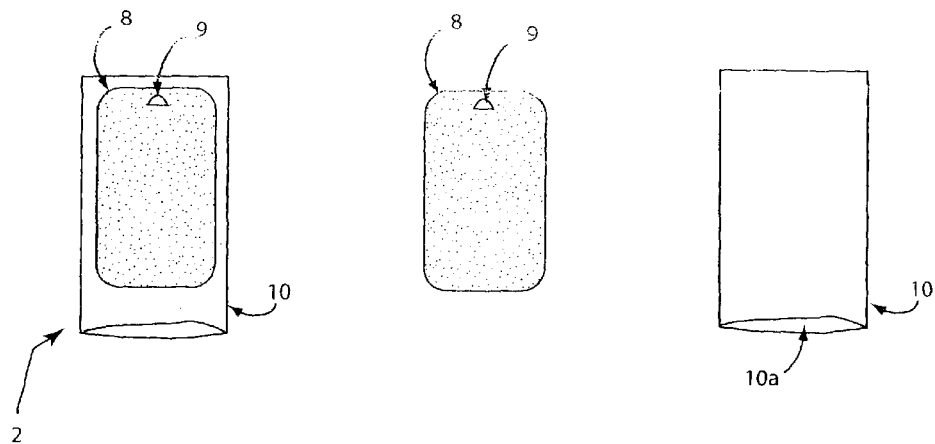
FIG. 2 illustrates an un-decorative blotter board, with a pre punched hole that is strung with an elastic loop for hanging, within a protective flow-wrapped plastic pouch, open at one end. The blotter board and protective flow-wrapped plastic pouch are also shown separately.
Figure 3:
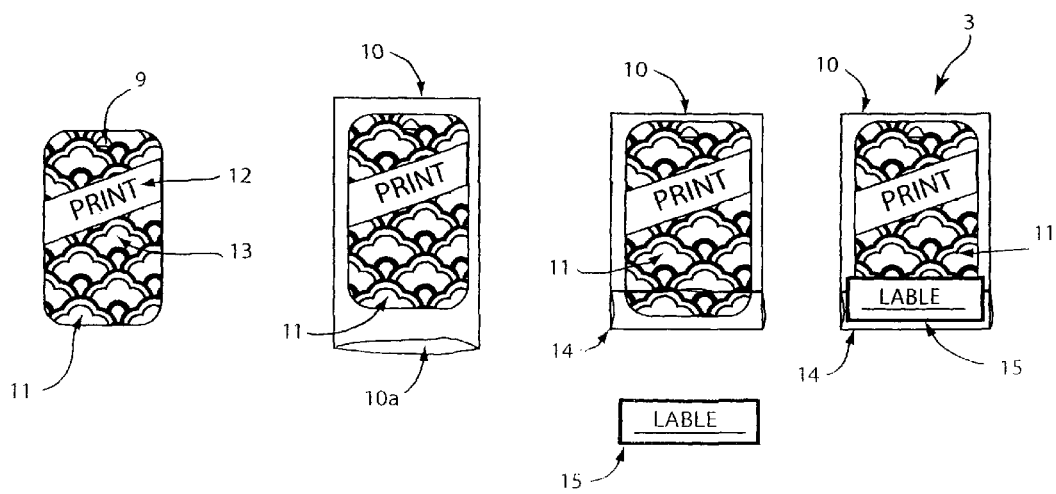
FIG. 3 illustrates a blotter board with decorative design and print applied, also referred to herein as a personalized decorative air freshener. Also illustrated is the personalized decorative air freshener contained within a flow-wrapped plastic pouch. The flow-wrapped plastic pouch is shown with an open end, and a flow to create a seal. Also shown is an adhesive label positioned to seal the flow-wrapped plastic pouch containing the personalized decorative air freshener.

Central to most air fresheners is an absorbent device to store and disperse the fragrance. A preferred example of an absorbent device is a blotter board 8 as shown in FIG. 2. The blotter board may be of any shape or size thereby allowing the individual to choose by aesthetic appeal. A preferred embodiment is a blotter board of rectangular shape of approximately 2⅞ by 4¼ inches and between 0.062 to 0.25 inches in thickness. In general usage the longitudinal sides are up right orientation by the user. Other shapes envisioned are polygons, triangles, and circles, as well as the shapes of plants, flowers, animals, or known characters including movie or cartoon characters. The blotter board typically has a means for support, preferably a hole through the blotter board 9, that may be pre strung with an elastic cord or string for hanging or for inserting a rigid support secured to a wall or upright fixture. Also shown in FIG. 2 is a flow-wrapped plastic pouch 10 for holding and protecting the blotter board before construction and/or after construction. The flow-wrapped plastic pouch 10 is preferably opened at one end 10a to facilitate removing and replacing the blotter board. As shown in FIGS. 1, 2 and 3, the flow-wrapped plastic pouch 10 may be used for storing the blotter board 8 before use 2, at any stage during construction, and/or after completion of the personalized decorative air freshener 3. As shown in FIG. 3, the personalized decorative air freshener 11 may be inserted into the flow-wrapped plastic pouch 10 through the open end 10a, and sealed by creating a fold 14 across the pouch near the open end 10a. As shown in FIG. 3, a preferred embodiment contains adhesive labels 15 that may be written on to identify completed air freshener 11, and/or used for sealing the flow-wrapped pouch 10. The flow-wrapped plastic pouch 10 may be sealed by placing the adhesive label 15 over the open end 10a, or placing the adhesive label 15 in position to secure the fold 14 near the open end 10a.

Figure 4:
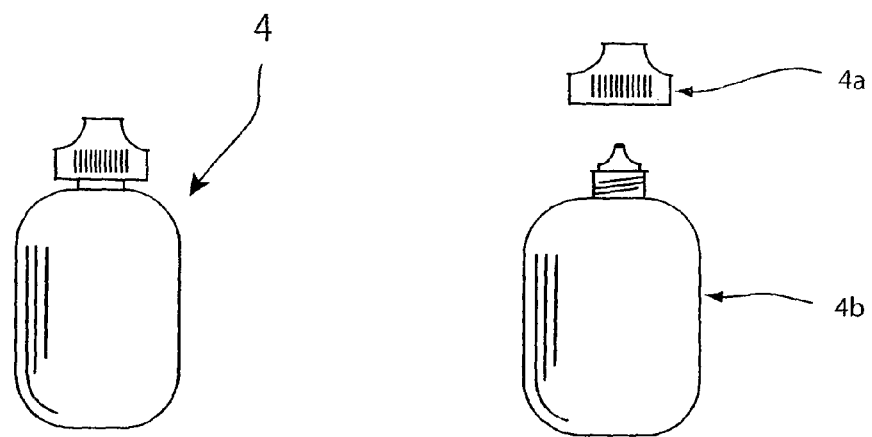
FIG. 4 illustrates one embodiment of a sealed container for fragrances. This embodiment consists of a dropper bottle and a re-sealable cap.

The kit includes fragrances in sealed containers 4, by way of example as shown in FIGS. 1 and 4, as a dropper bottle 4b with a resealable cap 4a. Resealable fragrance containers allow multiple applications of a particular fragrance. It is also envisioned that fragrances may be contained in single use disposable containers, for example, ampules, foil pouches, and vacuum formed sealed vials, whereby the entire contents of the container may be applied, and container discarded.

As children are among the expected users, non toxic child friendly fragrances and decorating materials are preferred. Non-toxic fragrances include those derived from natural sources and those which are flavored based. Included are naturals oils and fragrances extracted with water, steam, oil, or ethanol. Some solvents which are non-toxic or with low toxicity, such as ethanol or surfactants, may be acceptable. Some toxic components may be acceptable if present at low levels.

Examples of non-toxic fragrances include any and all fragrances or flavors associated with foods or nature. Non-limiting examples of foods include, apple pie, barbeque, birthday cake, chicken, fried chicken, donuts, French fries, hamburgers, hot dogs, ice cream, pizza, pop-corn and pumpkin. Non-limiting examples of fruits include apple, crabapple, hawthorn, pear, apricot, peach nectarines, plum, cherry, blackberry, raspberry, mulberry, strawberry, cranberry, blueberry, barberry, currant, gooseberry, elderberry, grapes, grapefruit, kiwi fruit, rhubarb, pawpaw, papaya, melon, watermelon, figs, dates, oranges, olive, jujube, pomegranate, lemon, lime key lime, mandarin, orange, sweet lime, tangerine, avocado, guava, kumquat, lychee, passion fruit, tomato, banana, gourd, and various melons.

Also included are fragrances of floral plants and spices. Non-limiting examples of floral fragrances include, azaleas, chamomile, chrysanthemum, clematis, corylopsis spicata, crab pyrus coronaria, flowering currant, garland flower, honeysuckle, iris, itea virginica, jasmine, lavender, lilacs, lilys, magnolia, olive, peony, phlox, primrose, pyrus angustifolia, rhododendron, ribes aureum, rose, rubus delicisus, sweet pea, wallflower, and yucca. Non-limiting examples of spices induce allspice, ajwain, anise, black cumin, black pepper, caraway seed, cardamom, cassia, cayenne, celery seeds, chile pepper, cinnamon, clove, coriander, cumin, dill, fennel, fenugreek, frankincense, galangal, garlic, ginger, horseradish, jalapeno pepper, juniper berries, licorice, mace, mustard, nutmeg, onion, paprika, peppercorns, saffron, sesame, star anise, sumac, Tabasco pepper, tamarind, and turmeric. Also included are bergamot, bitter gourd, blue gum, bottle gourd, carrot, carrot seed, cashew fruit, cacao, cedarwood, coconut, custard apple, cinnamon bark, clary sage, eucalyptus, frankincense, geranium, ginger, helichrysum italicum jasmine, lemon, jackfruit, lemongrass, mango, okra, Melissa, neem, oregano, otto, patchouli, peppermint, pineapple, rosemary, sandalwood, and vanilla.

As many fragrances are poorly soluble in water, in particular the essential oils, the addition of a carrier oil may prove beneficial in solubilizing the extracts. Non-toxic carrier oils are preferred. Examples of non-toxic carrier oils include, almond, apricot kernel, avocado, castor, cocoa butter, coconut/jojoba cream, coconut, evening primrose, grapeseed, hazelnut, hempseed, jojoba, kukui, rosehip seed, sesame sunflower, shea butter, and tamanu (foraha). By way of example, non-toxic fragrances may be made by mixing an essential oil with a base oil and adding water. As some fragrances are very difficult to solubilized in water, solvents, preferably low toxicity solvents such as ethanol, may be used as long as residual amounts of the solvent remaining in the final solution are low.

The kit may contain any number of instruments and materials useful for decorating the blotter board, for example, markers 5, crayons, pens, paint brushes 6, and containers of paints or dyes in a variety of colors 7, as shown in FIGS. 1 and 5. The markers, paints, and dyes are preferable odorless and non-reactive with the fragrances as well a suitable for drawing, writing, or coloring porous surfaces such as a blotter board. Markers include a marker pens, marking pens, or felt-tip pens, which typically have their own ink source and usually a tip made of porous pressed fibers such as felt or nylon. As children are among the expected users, non toxic child friendly markers, paints, and dyes are preferred. Non-toxic markers, paints, and dyes are those with no or very low levels of solvents, preferable solvents with low toxicity such as ethanol. Non-toxic paints and dyes may contain by way of example natural ingredients such as clay, chalk and talcum, milk casein, natural latex, bees' wax, earth, mineral dyes and are preferably water based.

The personalized decorative air freshener 11 may be constructed by any methods desired by the individual. Generally, the individual will begin by removing the blotter board 8 from the flow-wrapped plastic pouch 10, and on one or both sides of the blotter board, apply color and design 13 by painting or drawing with the decorative instruments 5, 6, and materials 7. The individual may apply any printing 12 the individual desires with markers 5, or pens or crayons. The individual will apply a fragrance, for example by adding drops of the fragrance to the blotter board from the sealed container 4. The construction of the personalized decorative air freshener described herein is exemplary only. The various steps such as the application of fragrance and decorating may be applied in any order. The individual may prefer to decorate to the blotter board when the surface is dry. Once completed the personalized decorative air freshener 11 may be inserted in to the flow-wrapped plastic pouch 10, through the open end 10a, and sealed by making a fold 14 across the pouch near the open end 10a. An adhesive label 15 may be applied to the flow-wrapped plastic pouch 10, through the open end 10a, and sealed by making a fold 14 across the pouch near the open end 10a. An adhesive label 15 may be applied to the flow-wrapped plastic pouch 10 to secure the fold 14 as shown in FIG. 3 Alternatively, the adhesive label 15 may be applied over the open end 10a to seal flow-wrapped plastic pouch 10. The individual may also write on the adhesive label to identify the particular personalized decorative air freshener.

Also envisioned are embodiments that contain pre-dyed, pre-cut, preprinted and/or de-bossed blotter boards. These may be designed around familiar themes, for example, birthdays, holidays, or popular movie or cartoon characters. In one embodiment is a kit designed to make personalized decorative Christmas tree ornament air fresheners. Also envisioned are preprinted blotter boards that may contain an open area for drawing and coloring or otherwise adding personalized writing, or images. Coloring may be suggested in a same manner similar to a child's coloring book.

Also envisioned are embodiments that include vacuum formed trays to facilitate applying the fragrance to the blotter board. A volume of fragrance solution may be added to a vacuum-formed tray and the blotter board immersed in the fragrance solution until a sufficient amount is absorbed.

In yet another embodiment, blotter board and flow-wrapped plastic pouches may be designed such that the fragrance is added to the blotter board while contained within the flow-wrapped plastic pouch. This may be accomplished by including a flow-wrapped plastic pouch with a re-sealable hole. The fragrance may then be applied to the blotter board, while inside the flow-wrapped plastic pouch, through the hole and then the hole resealed.

From the aforementioned description, a kit that is uniquely capable of enabling the average individual to construct a personalized decorative air freshener has been described. As such, those skilled in the art will appreciate that the conception upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

The invention claimed is:

1. A decorative air freshener that may be personally prepared, comprising:
    a kit for making a personalized decorative air freshener;
    said kit including a blotter board, said blotter board being of one of a rectangular, polygon, triangle, circle, plant shape, flower shape, characters and cartoon character shapes, and said blotter board being formed of an absorbent material to form an absorbent device in said kit;
    non-toxic decorating materials provided in said kit, said decorating materials including crayons, markers, pens, paints, and dyes in a variety of colors and provided in said kit within containers holding the decorating materials, said decorating materials capable of being applied to said blotter board during its preparation by the user;
    non-toxic fragrances in sealed containers provided in said kit, said fragrances being formed of natural oils, said fragrances extracted with water, steam, oil, and ethanol, to make the fragrances soluble, said non-toxic fragrances selected from the group including food aromas, floral plant aromas, spice aromas, candy aromas, all provided within sealed containers and which may be applied on to the blotter board during its formation by the user;
    a quantity of carrier oil and water to induce the fragrances to become soluble in said water when provided for application to the blotter board, said carrier oil and water including ethanol to make the fragrance more soluble in water; and
    an open ended flow-wrapped plastic pouch formed as a container and of the size to contain the fragrance applied blotter board, said pouch having a flap to seal and reseal the reusable pouch as the blotter board is prepared for usage.

2. The kit of claim 1, wherein said flow-wrapped plastic pouch is of the size to contain the absorbent material formed blotter board.

3. The kit of claim 1, and further comprising decorating instruments within said kit to provide for application of said decorating materials to the blotter board of the air freshener during its preparation.

* * * * *